United States Patent
Axelgaard

[19]
[11] Patent Number: 5,904,712
[45] Date of Patent: May 18, 1999

[54] CURRENT-CONTROLLING ELECTRODE

[75] Inventor: Jens Axelgaard, Fallbrook, Calif.

[73] Assignee: Axelgaard Manufacturing Co., LTD., Fallbrook, Calif.

[21] Appl. No.: 08/873,450

[22] Filed: Jun. 12, 1997

[51] Int. Cl.$^6$ .............................. A61N 1/04; A61B 5/04
[52] U.S. Cl. .................... 607/148; 607/149; 607/152; 600/391; 600/392; 600/393
[58] Field of Search .................... 607/148, 149, 607/152, 153; 600/391, 392, 393

[56] References Cited

U.S. PATENT DOCUMENTS

| | | | |
|---|---|---|---|
| Re. 31,454 | 12/1983 | Hymes | 128/641 |
| 4,067,342 | 1/1978 | Burton | 607/148 |
| 4,422,461 | 12/1983 | Glumac | 607/152 |
| 4,736,752 | 4/1988 | Munck et al. | 128/798 |
| 4,786,277 | 11/1988 | Powers et al. | 604/20 |
| 4,989,617 | 2/1991 | Memberg et al. | 128/785 |
| 5,038,796 | 8/1991 | Axelgaard et al. | 128/798 |
| 5,205,297 | 4/1993 | Montecalvo et al. | 128/798 |
| 5,215,089 | 6/1993 | Baker, Jr. | 128/642 |
| 5,265,608 | 11/1993 | Lee et al. | 128/642 |
| 5,331,966 | 7/1994 | Bennett et al. | 128/696 |
| 5,342,413 | 8/1994 | Hirschberg et al. | 607/126 |
| 5,356,428 | 10/1994 | Way | 607/142 |
| 5,366,497 | 11/1994 | Ilvento et al. | 607/142 |
| 5,372,125 | 12/1994 | Lyons | 128/640 |
| 5,423,871 | 6/1995 | Hoegnelid et al. | 607/28 |
| 5,423,877 | 6/1995 | Mackey | 607/117 |
| 5,425,751 | 6/1995 | Baeten et al. | 607/28 |
| 5,465,715 | 11/1995 | Lyons | 128/640 |
| 5,466,247 | 11/1995 | Scheiner et al. | 607/48 |
| 5,514,725 | 5/1996 | Mueller | 607/122 |
| 5,571,165 | 11/1996 | Ferrari | 607/152 |

Primary Examiner—Lee Cohen
Attorney, Agent, or Firm—Walter A. Hackler

[57] ABSTRACT

A transcutaneous medical electrode includes a highly conductive grid, having a plurality of arrays of electrical conductors, for controlling current distribution of directed electrical pulses. Electrical connectors are provided for establishing electrical communication with the conductive grid for enabling selective electrification of the electrical conductors in each array. The conductive grid is supported by a moderately conductive sheet, or film, and a conductive adhesive is provided for removably coupling the sheet or film and the conductive grid to a user's body.

30 Claims, 3 Drawing Sheets

CURRENT-CONTROLLING ELECTRODE

The present invention is generally related to transcutaneous electrodes and is more particularly directed to an electrode configuration for providing improved treatment of physical deficiencies such as, for example, joint swelling, tissue healing, muscle re-education, circulatory impairment, joint dysfunction, and postural disorders.

Nerve and muscle cells are excitable because they are able to discharge action potentials and, accordingly, electrical stimulation of nerve and muscle membranes can evoke such action potential. In order for an action potential to be evoked, the stimulus intensity and pulse duration must be sufficient to pass a threshold. In this regard, muscle membranes require longer pulse durations due to their higher capacitance. Thus, in order to meet this threshold, transcutaneous electrodes must not only be properly placed on the skin but coupled thereto in order to provide sufficient current density to a particular cross-sectional area body tissue current density. This is a very important factor in controlling the reaction of biological tissue to stimulation. As a rule, the greater the current density, the greater the resulting reaction on the tissue.

Earlier electrodes, such as set forth in U.S. Pat. No. 4,736,752, teach the control of current density across an electrode through the use of a conductive ink design area.

Electrode placement is another factor that influences current density and, accordingly, tissue response. This is due to the fact that the impedance of skin, bone, and adipose tissue vary, and, accordingly, placement of electrodes over these tissues will have significant effect on current flow in the surrounding tissues. In addition, orientation of the electrodes can also significantly affect the response of underlying tissue. For example, muscle tissue is nearly four times more conductive in the longitudinal direction of their fibers than in the transverse direction.

In addition, current density at the electrode-tissue interface also depends on the electrode configuration, its ability to conform to a body part, body inflexibility, and a coupling agent to provide low impedance contact between the electrode and the skin surface.

It is accordingly often desirable to provide means for dynamically controlling the current density provided by an electrode. Such dynamic control would enable accommodation not only for misplacement of the electrode in an area designated for stimulation but also to maximize biological response to current pulses provided by the electrode. As hereinabove noted, insufficient current may not cause the expected physiological response. Thus efficient design of current density eliminates unnecessary current which may increase patient discomfort and decrease the efficiency of the electrode.

The present invention is directed to an electrode system which features control of current density which not only enables the electrode to be optimized for current density for a specific application to a tissue but also accommodates for inaccuracies made in placing the electrode upon a skin surface. A further embodiment of the present invention enables sequential control of current density to enhance the treatment of various physical deficiencies.

SUMMARY OF THE INVENTION

A transcutaneous medical electrode, in accordance with the present invention, generally includes an electrically conductive grid means having a plurality of arrays of electrical conductors for controlling current distribution of directed electrical pulses, along with means for establishing the electrical communication with the conductive grid means for enabling selective electrification of the electrical conductors in each array. By selective electrification of the conductors, the current density of the electrode is controlled and varied over an area of the electrode. This facilitates the optimization of the current density of the electrode which can accommodate for misplacement of the electrode on the skin of a patient and maximize coupling of the pulses with the underlying tissue. In this embodiment of the present invention, means are also provided for supporting the electrically conductive grid means and means for removably coupling the means for supporting the electrically conductive grid means to a body on skin tissue.

More particularly, the electrode, in accordance with the present invention, may include a flexible conductive sheet along with conductive adhesive means disposed on one side of the flexible conductive sheet for electrically coupling the flexible conductive sheet to a user's body. Conductive grid means are provided and disposed on another side of the flexible conductive sheet for controlling current distribution through the conductive sheet and the conductive adhesive and into the user's body. In this embodiment, the conductive grid may comprise at least one array of conductive ink lines. In addition, means are provided for establishing an electrical connection with the conductive grid means.

More specifically in this embodiment, the conductive grid means may comprise a plurality of arrays of conductive ink lines, and the electrode may further comprises insulation means, disposed between the arrays, for preventing electrical communication between the arrays. This feature enables isolated electrification of the arrays and provides for the layered electrode which can more effectively enable the placement of multiple electrodes on the surface than is possible with separate discrete electrodes. This combination not only is effective for controlling current density at a specific site but for progressively effecting stimulation on a progressively moving site, as will be hereinafter described in greater detail.

The present invention provides conductive grid means which includes a plurality of arrays with conductive ink lines, with each of the plurality of arrays, at least in part, overlapping one another, and the means for establishing electrical connection comprises at least one lead wire connected with each of the plurality of arrays for enabling selective electrification of a group of arrays, in order to change the current density through the flexible conductive sheet and the conductive adhesive.

In another embodiment of the present invention, the electrode includes a conductive grid which is comprised of a plurality of conductive ink spots, or dots, and the means for establishing electrical communication comprises lead wire means connected with each of the conductive ink spots for enabling selective electrification of at least one conductive ink spot in order to change the current density through the flexible conductive sheet and the conductive adhesive. In this manner, any combination of the ink spots will be electrified to provide customization of the current density provided by the electrode. In addition, the individual conductive ink spots make this embodiment of the present invention amenable for digital control, i.e., each of the dots may be separately electrified in order to create various desired patterns to effect a desired current density suitable for specific underlying tissue.

In yet another embodiment of the present invention, the conductive grid means of the electrode includes a plurality of arrays of conductive ink lines with the arrays overlying one another in a longitudinal direction, enabling sequential electrification of each array along the longitudinal direction. This, in turn, enables electrical stimulation to be applied to the user's body to effect sequential peristaltic-like stimulation of underlying muscles.

In still another embodiment of the present invention, the electrode includes arrays of conductive grids in a rectangular pattern for enabling sequential or simultaneous electrification of the arrays to control the current distribution in a rectilinear pattern.

The present invention further includes the improvement of any suitable transcutaneous medical electrode for directing pulses into a user's body with the improvement including an electrically conductive grid means having a plurality of arrays of electrical conductors for controlling current distribution of the directed electrical pulses, and means for establishing electrical communication with the electrical grid means for enabling selective electrification of the electrical conductors in each array.

The present invention further encompasses a method for administering electrical pulses to a user's body which includes the steps of electrically coupling an electrode having a plurality of conductive grids therein to a user's body with a conductive adhesive and thereafter sequentially electrifying the conductive grids to stimulate underlying muscles in a peristaltic-like manner.

Also encompassed by the present invention is a method for administering electrical pulses to a user's body which includes the steps of electrically coupling an electrode having a plurality of conductive grids therein to a user's body with a conductive adhesive and providing electrical pulses to at least one of the conductive grids to stimulate an underlying muscle. Further, the method includes sensing an electrical signal generated by the underlying muscle and in response thereto providing electrical pulses to at least another of the conductive grids. This procedure is iterated to a maximum signal strength and sent; thereafter, electrical pulses are provided to the conductive grid or grids which result in the maximum sent signal. In this manner, the present invention provides for a biofeedback method of administering electrical pulses to a user's body which is self-correcting, or self-optimizing, thereby significantly improving the efficiency of the electrodes utilized.

BRIEF DESCRIPTION OF THE DRAWINGS

The advantages and features of the present invention will appear from the following description when considered in conjunction with the accompanying drawings in which.

DETAILED DESCRIPTION

Figure 1:
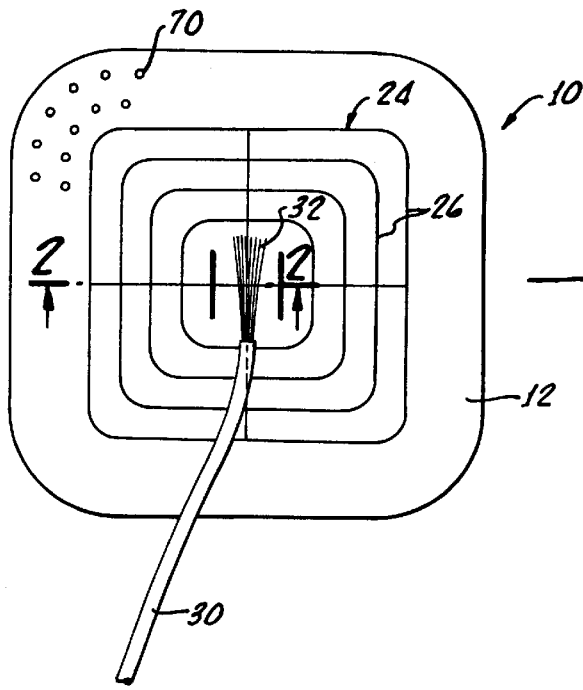
FIG. 1 is a plan view of the transcutaneous medical electrode, in accordance with the present invention, showing a representative conductive grid means disposed on a conductive sheet for controlling current distribution.

Turning now to FIG. 1, there is shown an electrode 10 in accordance with the present invention which generally includes a flexible conductive sheet 12 which may be formed from any suitable carbon loaded elastomeric film having suitable surface resistivity of between about $10^3$ ohms/square and about $10^4$ ohms/square, for example, about 5000 ohms/square and a transverse resistivity of between about $10^3$ and about $10^5$ ohms/square, for example, about $10^4$ ohms/square. Suitable polycarbonate, polyolefin and polyvinylchloride films are available from, for example, 3-M Manufacturing Company and Rexam Graphics. A conductive adhesive 14 disposed on one side 18 of the conductive sheet 12 provides a means for electrically coupling the flexible conductive sheet 12 to a user's body (not shown in FIGS. 1 and 2). Any suitable conductive adhesive may be utilized such as those manufactured by Valleylab, Inc., Boulder, Colo. or ProCam Medical, Chicopee, Mass.

Disposed on another side 20 of the conductive sheet 12 is a highly conductive grid 24 which provides means for controlling current distribution through the flexible conductive sheet 12 and the conductive adhesive 14 into a user's body. The conductive grid 24 may be formed with conductive ink lines 26 applied to the conductive sheet 12. The conductive lines may be formed from any suitable blend of inks including carbon, metals such as silver or copper.

It should be appreciated that the conductivity of the conductive grid 24, i.e., ink lines 26, is much greater than the conductivity of the flexible conductive sheet 12, which is moderately conductive, in order to control the current distribution through the conductive sheet 12. For example, with a surface resistivity of about 5000 ohms/square and a transverse resistivity of about $10^4$ for the sheet 12, the resistivity of the ink lines should be about 1 to about 10 ohms/cm.

The difference in conductivity or resistivity between the sheet 12 and the lines 26 enables precise control of current distribution which cannot be achieved, for example, with a non-conductive sheet or a highly conductive sheet. In fact, ink lines 26 of varied conductivity may be utilized in order to tailor the current through the conductive sheet which may have a thickness of up to about 3 mils, for example, about 1 mil.

Electrification of the conductive grid 24 is provided by a lead wire 30 which provides a means for establishing electrical connection with the conductive grid 24 and the individual conductive ink lines 26 therein.

Figure 2:
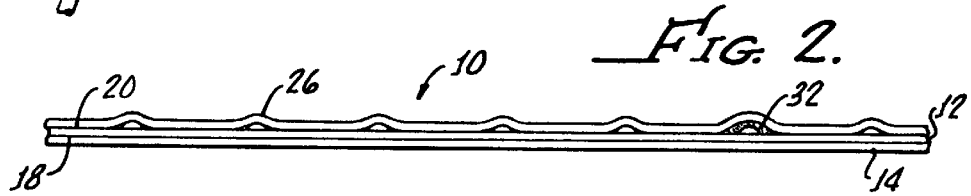
FIG. 2 is a cross-section of the electrode shown in FIG. 1 taken along a line 2—2, showing a flexible conductive sheet, a conductive adhesive applied on one side of the flexible conductive sheet, and a conductive grid disposed on another side of the flexible conductive sheet.
Figure 3:
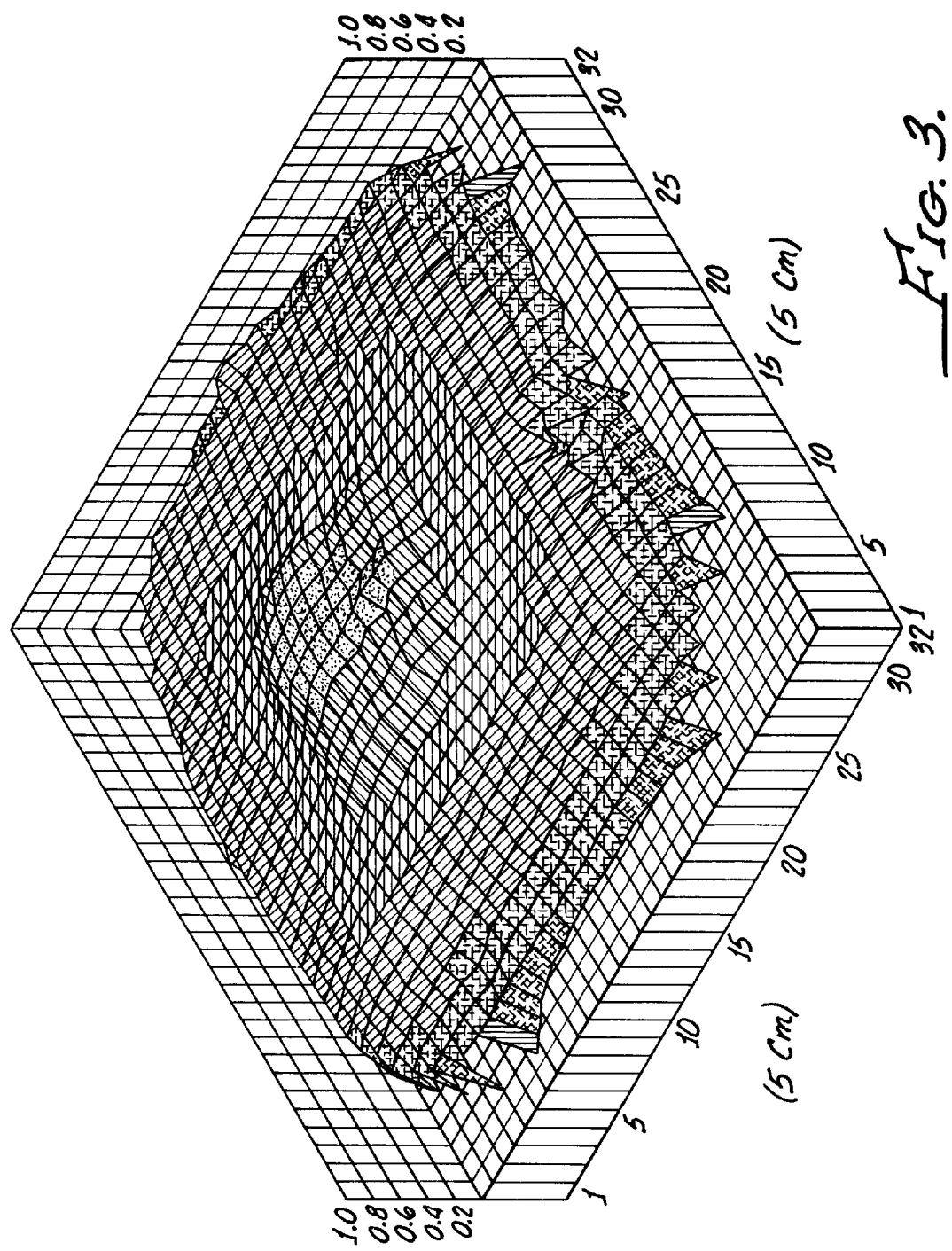
FIG. 3 is a representation of the current density achieved across a skin surface utilizing the electrode shown in FIG. 1.

The electrode 10, in accordance with the present invention, is clearly distinguishable over U.S. Pat. No. 4,736,752, which utilized a conductive ink grid on a non-conductive flexible backing sheet, such as polyethylene or the like. The present invention utilizes a conductive sheet onto which additional conductive ink lines are disposed, or printed, in order to provide and control a current distribution through the flexible conductive sheet 12 and adhesive 14 into a user's body. In that regard, current distribution provided by the electrode 10 shown in FIG. 1 provides a current distribution over its 5 cm sides, as shown in FIG. 3, which illustrates in three-dimensional format the normalized current distribution and the uniformity achieved by the electrode 10 made in accordance with the present invention. Utilization of the conductive sheet provides yet another element of current distribution controlled, not anticipated by the prior art such as U.S. Pat. No. 4,736,752. The width and thickness of the lines 26, as shown in FIG. 2, may also be utilized to further control the current density provided by the electrode 10. Strands, or filaments, 32 of lead wire 30 may be adhered or press-fit to the conductive grid 24 in any conventional manner.

Figure 4:
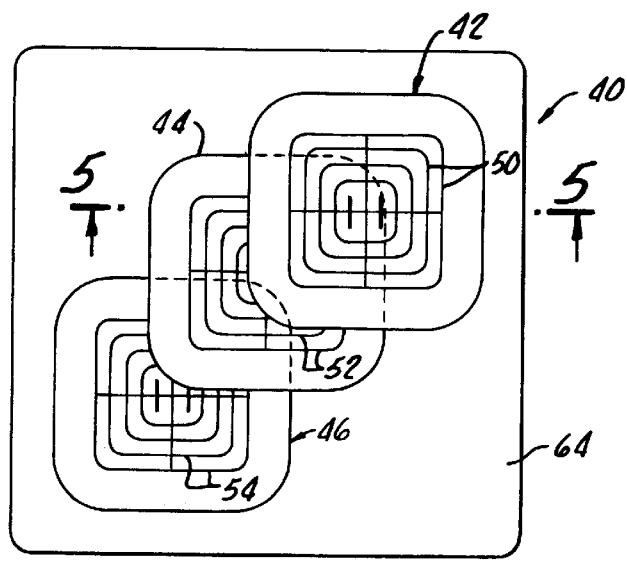
FIG. 4 is a plan view of an electrode utilizing overlying arrays of conductive grids in a rectilinear pattern for enabling sequential or simultaneous electrification of the arrays to control the current distribution in a rectilinear manner.
Figure 5:
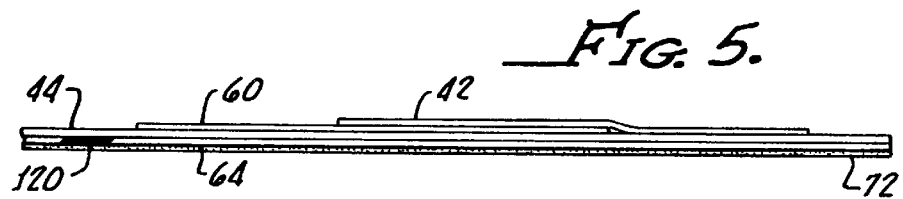
FIG. 5 is a cross-sectional view of the electrode shown in FIG. 4 taken along the line 5—5.

Importantly, electrode 10 provides a building block, or element, for electrode 40, for example, as illustrated in FIG. 4. In the electrode 40 a plurality of arrays 42, 44, 46 of conductive ink lines 50, 52, 54 is provided, which lines may overlap one another and which may include insulation layers 60 disposed between arrays 42, 44, as shown in FIG. 5 disposed on a flexible conductive sheet 64. The insulation layer 60 may be formed from any suitable non-conductive sheet material such as, for example, polyethylene, and the thickness of the insulation layer 60 as well as the conductive sheets, 12, 64, may be 3 mm or less in order to provide sufficient flexibility of the electrodes 40, 44 conforming to various body contours. It should be appreciated that perforations, or holes, 70 may be provided in a non-conductive sheet, as necessary, in order to increase the flexibility thereof to provide desired conformity to various body parts. Both the perforation 70, and placement thereof, will of course be dependent upon electrode 10, for the size, as well as the thickness of the films involved, 64, and insulation layers 60.

It should also be appreciated that in a number of different grid 24, 42, 44, 46 patterns may be utilized to tailor the distribution. In this regard, the patterns shown in U.S. Pat. No. 4,736,752 are incorporated herewith in the present application for showing of various grid patterns which may be suitable for use in the present invention. Also, it should be noted that no lead wires are shown in FIGS. 4 and 5 for the sake of clarity in showing the arrangement of the grid patterns 42, 44, 46 on the conductive sheet 64. These lead wires, as shown specifically for one array or grid 24, illustrated in FIG. 1, provide a means for establishing electrical connection with each of the plurality of grids, or arrays 42, 44, 46, which enable selective electrification of one or more or a group of arrays in order to change the current density through the flexible conductive sheet 64 and conductive adhesive 72.

As shown in FIG. 4, the plurality of arrays 42, 44, 46 and conductive lines 50, 52, 54 may be disposed with each of the plurality of arrays 42, 44, 46 overlapping, at least in part, with one another. When arranged in a rectangular pattern, as shown in FIG. 4, the arrays 42, 44, 46 enable sequential or simultaneous electrification in a rectilinear manner.

Importantly, one of the arrays 42 may be utilized as a sensor for electrical signals generated by an underlying muscle (not shown in FIG. 4) in order to provide a method for administering electrical pulses to a user's body, as will be hereinafter described in greater detail.

Figure 6:
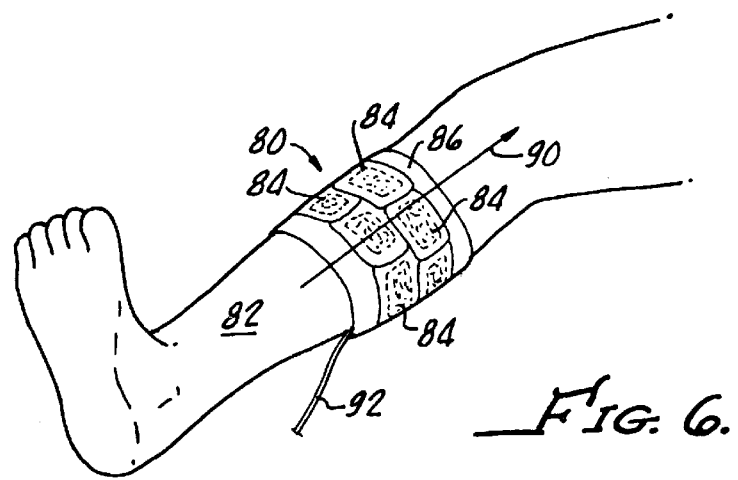
FIG. 6 is another embodiment of the present invention in which conductive grid arrays are overlaid on one another in a longitudinal direction for enabling electrical stimulation to be applied to a user's body to effect sequential peristaltic-like stimulation of underlying muscles.

Turning now to FIG. 6, there is shown an alternative embodiment 80, in accordance with the present invention, as it may be disposed on a leg 82 of a user, which includes a plurality of arrays, or grids, 84 disposed on a conductive film 86, as hereinabove described in connection with the embodiments 10 and 40, shown in FIGS. 1 through 5, except that the arrays overlie each other in a longitudinal direction shown by the arrow 90, so that selective electrification through the lead 92 interconnecting each of the arrays 84 may be provided in a sequential timing manner along the longitudinal direction 90 in order to effect a sequential peristaltic-like stimulation of underlying muscles (not shown).

It should be appreciated that the position of the electrode 80 on the leg 82 is only shown for illustration purposes and the full utilization of the electrode 80 made in accordance with the present invention is not limited thereto, but is suitable for application on any body part on which peristaltic-like stimulation of underlying muscles would be beneficial.

Figure 7:
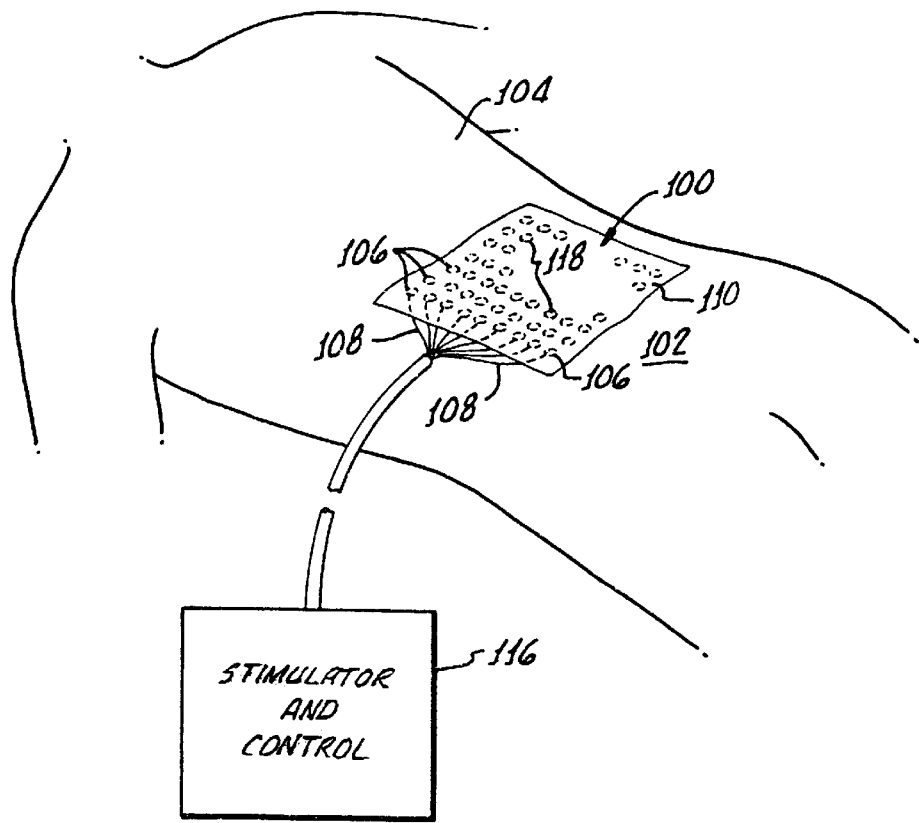
FIG. 7 illustrates an electrode in accordance with the present invention with a plurality of conductive spots for enabling selective electrification in order to change the current density across the electrode.

Turning now to FIG. 7, there is yet another embodiment 100, in accordance with the present invention, disposed on a lower back portion 102 of the user 104. In this embodiment, a plurality of conductive ink spots 106 is provided with each spot 106 interconnected with a lead 108 for enabling selective electrification of at least one conductive ink spot 106, in order to change the current density through a conductive film or sheet 110 and conductive adhesive (not shown), utilized to adhere the electrode 100 to the user 104. Electrification of each combination of conductive ink spots 106 is provided by a stimulator and control device 116 which may be any suitable electric/electronic device known in the art for providing electrical pulses for stimulation. In addition, one or more of the conductive ink spots 118 may be utilized as a receiver of electrical signals so that the electrical pulse is provided to adjacent conductive ink spots 106 and may be altered in order to provide stimulation to underlying muscles which results in a maximum sense to signal from the receptors 118.

Turning now to FIG. 5, any of the electrodes 10, 40, 100, in accordance with the present invention, may incorporate a reservoir 120 of a therapeutic agent suitable for iontophoresis which is disposed in an operative relationship with one of the arrays 54 of the conductive ink lines 46. This operative relationship may be embedding the agent within the film or separately supporting the agent in order that electrical pulses from the grid 46 may operate through or transfer the active agent into the skin of a patient, as is well-known in the iontophoresis art. Thus, while other conductive grids 42, 44 may be utilized for specific treatment through transcutaneous pulses, the grid 46 may be utilized to separately transfer a therapeutic agent into the skin as may be desired for either treatment of a condition or for anesthetizing surface portions of the body.

The present invention, through the use of the hereinabove described electrode 80, provides a method for administering electrical pulses to a user's body with the method including the steps of electrically coupling an electrode 80 having a plurality of conductive grids 84 therein to a user's body, and thereafter sequentially electrifying the conductive grids 84 to stimulate underlying muscles in a peristaltic-like manner.

A method in accordance with the present invention for administering electrical pulses through a user's body utilizing electrodes 40, 100 includes the steps of electrically coupling the electrodes 40, 100 having a plurality of conductive grids 42, 44, 46, or spots 106, to a user's body and thereafter providing electrical pulses to at least one of the conductive grids 42, 44, 46, or spots 106, to an underlying muscle. An electrical signal generated by the underlying muscle is sensed and in response thereto, electrical pulses are provided to at least another of the conductive grids 42, 44, 46 or spots 106. This procedure is iterated until a maximum electrical signal is sensed and thereafter electrical pulses are provided to the conductive grid, spots, or grids, which results in the maximum sent sensed signal. Thus, the electrode is able to optimize its delivery of pulses by selection of electrification of grids 42, 44, 46 or spots 106.

Although there has been hereinabove described specific transcutaneous medical electrodes and methods in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A transcutaneous medical electrode comprising:
   a flexible conductive sheet;
   conductive adhesive means, disposed on one side of said flexible conductive sheet, for electrically coupling said flexible conductive sheet to a user's body;
   conductive grid means, disposed on another side of said flexible conductive sheet, for controlling current distribution through the flexible conductive sheet and conductive adhesive means and into the user's body, said conductive grid means comprising
   a plurality of arrays of conductive ink lines;
   insulation means, disposed between the arrays, for preventing electrical communication between the arrays; and
   means for establishing electrical connection with said conductive grid means.

2. The electrode according to claim 1 wherein each of the plurality of arrays, at least in part, overlapping one another, and the means for establishing electrical connection comprises at least one lead wire means, connected with each of the plurality of arrays, for enabling selected electrification of a group of arrays in order to change the current density through the flexible conductive sheet and conductive adhesive, said group consisting of at least two of said arrays of conductive ink lines.

3. The electrode according to claim 1 wherein each of the plurality of arrays, at least in part, overlapping one another and the means for establishing electrical connection comprises lead wire means, connected with each of the plurality of arrays, for enabling selected electrification of at least one of the arrays in order to control the current density through the flexible conductive sheet and conductive adhesive.

4. The electrode according to claim 1 wherein the means for establishing electrical connection comprises lead wire means, connected with each conductive ink line, for enabling selected electrification of at least one conductive ink line in order to change the current density through the flexible conductive sheet and conductive adhesive.

5. The electrode according to claim 1 wherein each array of conductive ink lines overlays, at least in part, another array.

6. The electrode according to claim 5 wherein the arrays overlay one another along a longitudinal direction along the arrays for enabling sequential electrification of each array along the longitudinal direction.

7. The electrode according to claim 5 wherein the arrays overlay one another in a rectangular pattern for enabling sequential or simultaneous electrification of the arrays to control the current distribution in a rectilinear manner.

8. The electrode according to claim 1 further comprising a reservoir of a therapeutic agent suitable for iontophoresis disposed in an operative relationship with one of the arrays of conductive ink lines.

9. A transcutaneous medical electrode comprising:
   a flexible conductive sheet;
   conductive adhesive means, disposed on one side of said flexible conductive sheet, for electrically coupling said flexible conductive sheet to a user's body;
   conductive grid means, disposed on another side of said flexible conductive sheet, for enabling electrical stimulation to be applied to the user's body to effect a sequential stimulation of underlying muscles; and
   means for establishing electrical connection with said conductive grid means.

10. The electrode according to claim 9 wherein said conductive grid means comprises at least one array of conductive ink lines.

11. The electrode according to claim 9 wherein said conductive grid means comprises a plurality of arrays of conductive ink lines.

12. The electrode according to claim 11 wherein each one of the arrays of conductive ink lines at least partially overlays another one of the arrays of conductive ink lines.

13. The electrode according to claim 12 wherein the means for establishing electrical connection comprises at least one lead wire connected to each of the arrays.

14. The electrode according to claim 12 further comprising insulation means, disposed between overlaying conductive ink lines, for preventing electrical communication between the arrays of conductive ink lines.

15. A transcutaneous medical electrode comprising:
   a flexible conductive sheet;
   conductive adhesive means, disposed on one side of said flexible conductive sheet, for electrically coupling said flexible conductive sheet to a user's body;
   conductive grid means, disposed on another side of said flexible conductive sheet, for directing electrical pulses into the user's body and for receiving electrical signals from the user's body, said conductive grid means comprising at least one array of conductive ink lines for directing electrical pulses in the user's body and at least another array of conductive ink lines for receiving electrical signals from the user's body; and
   means for establishing electrical connection with said conductive grid means.

16. The electrode according to claim 15 wherein said conductive grid means comprises a plurality of conductive ink lines for directing electrical pulses into the user's body and a plurality of conductive ink lines for receiving electrical signals from the user's body, and the means for establishing electrical connection comprises lead wire means, connected with each conductive ink line, for enabling selected electrification of conductive ink lines in response to electrical signals received by other conductive ink lines.

17. The electrode according to claim 16 further comprising multiple arrays of the conductive ink lines, and each one of the arrays of conductive ink lines at least partially overlays another one of the arrays of ink lines.

18. The electrode according to claim 17 further comprising insulation means, disposed between overlaying conductive ink lines for preventing electrical communication therebetween.

19. A transcutaneous medical electrode comprising:
   electrically conductive grid means, having a plurality of arrays of electrical conductors, for controlling current distribution of directed electrical pulses;
   means for establishing electrical communication with said conductive grid means, the means for establishing communications comprising electrical connector means, connected with each array, for enabling selective electrification of the electrical conductors in each array;

means for supporting said electrically conductive grid means; and means for removably coupling the means for supporting said electrically conductive grid means to a user's body.

20. The electrode according to claim 19 wherein the electrical conductors of each array overlays, at least in part, electrical conductors of another array.

21. The electrode according to claim 20 wherein said electrical conductors overlay one another along a longitudinal direction along the arrays for enabling sequential electrification of each array along the longitudinal direction.

22. The electrode according to claim 20 wherein said electrical conductors overlay one another in a rectangular pattern for enabling sequential or simultaneous electrification of the electrical conductors to control the current distribution in a rectilinear manner.

23. The electrode according to claim 19 further comprising a reservoir of a therapeutic agent suitable for iontophoresis disposed in an operative relationship with at least one of the arrays of electrical conductors.

24. In a transcutaneous medical electrode for directing electrical pulses into a user's body, an improvement comprising:

electrically conductive grid means, having a plurality of arrays of electrical conductors, for controlling current distribution of the directed electrical pulses; and means for establishing electrical communication with said conductive grid means, the means for establishing communications comprising electrical connector means, connected with each array, for enabling selective electrification of the electrical conductors in each array.

25. The improvement according to claim 24 wherein the electrical conductors of each array overlays, at least in part, electrical conductors of another array.

26. The improvement according to claim 25 wherein said electrical conductors overlay one another along a longitudinal direction along the arrays for enabling sequential electrification of each array along the longitudinal direction.

27. The improvement according to claim 25 wherein said electrical conductors overlay one another in a rectangular pattern for enabling sequential or simultaneous electrification of the electrical conductors to control the current distribution in a rectilinear manner.

28. A method for administering electrical pulses to a user's body, the method comprising the steps of:

electrically coupling an electrode having a plurality of conductive grids therein to a user's body with a conductive adhesive; and sequentially electrifying the conductive grids to stimulate underlying muscles in a sequential manner.

29. A method for administering electrical pulses to a user's body, the method comprising the steps of:

(a) electrically coupling an electrode having a plurality of conductive grids therein to a user's body with conductive adhesive;

(b) providing electrical pulses to at least one of the conductive grids to stimulate an underlying muscle;

(c) sensing an electrical signal generated by the underlying muscle;

(d) in response to the sensed signal, providing electrical pulses to at least another of the conductive grids;

(e) repeating steps (c)–(d) until a maximum electrical signal is sensed; and (f) thereafter continuing to provide electrical pulses to the conductive grid or grids which results in the maximum sensed signal.

30. The method according to claim 29 wherein the step of sensing the electrical signal includes using at least one of the conductive grids in the coupled electrode for sensing.

* * * * *